United States Patent [19]

Bashir-Hashemi

[11] Patent Number: 5,378,333
[45] Date of Patent: Jan. 3, 1995

[54] HALOGENATED POLYCARBOXYCUBANES

[75] Inventor: Abdollah Bashir-Hashemi, Bridgewater, N.J.

[73] Assignee: The United States of America as represented by the Secretary of the Army, Washington, D.C.

[21] Appl. No.: 28,709

[22] Filed: Mar. 5, 1993

[51] Int. Cl.⁶ .............................................. C07C 23/00
[52] U.S. Cl. .................... 204/157.65; 204/157.87; 204/157.89; 204/157.94; 560/114; 560/116
[58] Field of Search ................ 562/497, 498; 560/114, 560/116; 204/157.87, 157.89, 157.65, 157.94

[56] References Cited

U.S. PATENT DOCUMENTS

| | | | |
|---|---|---|---|
| 3,418,368 | 12/1968 | Dunn et al. | 560/116 |
| 3,517,055 | 6/1970 | Loeffler | 560/116 |
| 3,551,576 | 12/1970 | Loeffler | 562/498 |
| 5,214,221 | 5/1993 | Bashir-Hashemi | 568/944 |
| 5,214,222 | 5/1993 | Bashir-Hashemi | 568/945 |

OTHER PUBLICATIONS

March, Jerry. *Advanced Organic Chemistry: Reaction, Mechanism, and Structure* 3rd edition, John Wiley & Sons, 1985, pp. 620–621.
Cubanes: Starting Materials for the New Century, Agnew Chem. Int. Engl. 1992, 31 1423.

*Primary Examiner*—Robert L. Stoll
*Assistant Examiner*—Valerie Fee
*Attorney, Agent, or Firm*—Edward Goldberg; Michael C. Sachs; John E. Callaghan

[57] ABSTRACT

The disclosure describes photochemical synthesis of halogenated polycarboxycubanes from simple carboxycubanes and an oxalyl halide. It is possible to synthesize 6-Chloro-1,2,4,7-tetracarbomethoxycubane and 2-Chloro-1,3,5,7-tetracarbomethoxycubane. Photochemical synthesis of halogenated polycarboxycubanes from carboxy cubane and an oxalyl halide is reported.

3 Claims, No Drawings

HALOGENATED POLYCARBOXYCUBANES

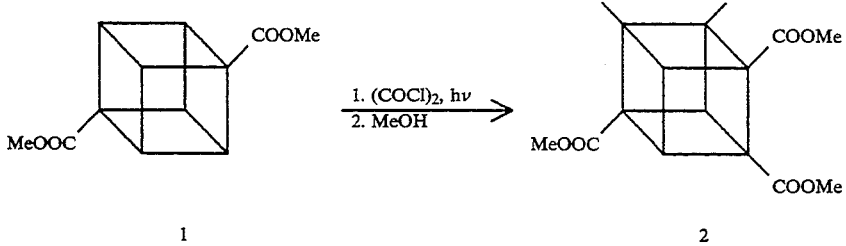

1 → 2

GOVERNMENTAL INTEREST

The Government has rights in this invention pursuant to Contract No. DAAA21-89-C-0013 awarded by the U.S. Army.

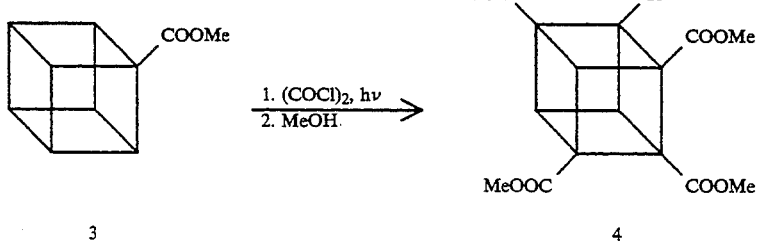

3 → 4

The invention described herein may be manufactured, used and licensed by or for the U.S. Government.

FIELD OF USE

This invention described an efficient, photochemical synthesis of halogenated polycarboxycubanes from the reaction of commercially-available precursors with an oxalyl halide.

BACKGROUND OF THE INVENTION

There has been renewed interest in the chemistry of cubane since some of its derivatives, particularly nitrocubanes, have shown promise as high density energetic materials. The exceptional strain energy (166 kcal/mol) and rigid framework of the cubane skeleton also suggest promise for the use of substituted cubanes in the fields of pharmaceuticals and polymers (Chemistry of Energetic Materials; Ed., G. A. Olah; D. R. Squire; Academic Press, Inc., San Diego, Calif., 1991. Also see Carbocyclic Cage Compounds; Ed., E. J. Osawa; O. Yonemitsu; VCH Publishers, Inc., New York, N.Y., 1992).

Although several synthetic methods have been applied for the synthesis of halogenated cubanes, however, direct halogenation of the cubane systems bearing electron-withdrawing substituents such as carboxy or nitro groups has not been documented.

The present report described the photochemical synthesis of halogenated polycarboxycubanes from simple carboxycubanes and an oxalyl halide.

SUMMARY OF THE INVENTION

The starting material for this synthesis was 1,4-dicarbomethoxycubane which is commercially-available from Enichem, Italy. A solution of 1,4-dicarbomethoxycubane 1 in oxalyl chloride was photolyzed under a sunlamp at 60° C. The excess oxalyl chloride was recovered under reduced pressure. The resulting crude product was treated with methanol and 6-chloro-1,2,4,7-tetracarbomethoxycubane 2 was isolated.

In another experiment when monocarbomethoxycubane 3 was reacted with oxalyl chloride under sunlamp for 36 h at 60° C., after esterification with methanol, 2-chloro-1,3,5,7-tetracarbomethoxycubane 4 was obtained.

DESCRIPTION OF THE PREFERRED EMBODIMENTS

The following section describes specific experimental procedures used for the synthesis:

A mixture of 1,4-dicarbomethoxycubane 1 (440 mg, 2.0 mmol) in oxalyl chloride (50 mL) was photolyzed under a sunlamp at 60° C. for 48 h. $^1$H NMR of the reaction mixture showed no trace of the remaining starting material. The excess oxalyl chloride was removed on a rotary evaporator, and the residue was stirred with dry MeOH (50 mL) at room temperature for 3 h. The mixture was concentrated and the oily residue was taken up into EtOAc (30 mL), washed with 5% aqueous $Na_2CO_3$ then brine and dried ($Na_2SO_4$). After removing the solvent under reduced pressure, the crude product was chromatographed using silica gel and hexane/$CH_2Cl_2$ (5:1) as eluent to give 6-chloro-1,2,4,7-tetracarbomethoxycubane 2; m.p. 134°–135° C.; $^1$HNMR (CDCl$_3$); δ4.68 (m, 1H), 4.54 (dd, 1H), 4.42 (dd, 1H); 3.80 (s, 6H); 3.78 (s, 6H)ppm.

Similarly, the reaction of monocarbomethoxycubane 3 (162 mg, 1 mmol) with oxalyl chloride (15 mL) under a sunlamp at 60° C. for 36 h, followed by esterification with methanol and the aforesaid workup, yielded 2-chloro-1,3,5,7-tetracarbomethoxycubane 4; m.p. 178°–180° C.; $^1$HNMR (CDCl$_3$); δ4.65 (s, 3H); 3.80 (s, 9H); 3.75 (s, 3H) ppm.

What is claimed is:

1. 6-Chloro-1,2,4,7-tetracarbomethoxycubane.
2. 2-Chloro-1,3,5,7-tetracarbomethoxycubane.
3. A method for the photochemical halogenation of a cubane skeleton comprising the steps, a) selecting a cubane selected from the group consisting of 1,4 dicarbomethoxycubane 1 and monocarbomethoxycubane 3, b) adding the cubane to oxalyl chloride to form a mixture, c) subjecting the mixture to ultra violet irradiation for sufficient period of time to complete the halogenation, and d) recovering the halogenated cubane.

* * * * *